US00PP26789P2

(12) United States Plant Patent
Danziger

(10) Patent No.: US PP26,789 P2
(45) Date of Patent: May 31, 2016

(54) ***SUTERA* PLANT NAMED 'DANOVA780'**

(50) Latin Name: *Sutera cordata*
Varietal Denomination: Danova780

(71) Applicant: Gabriel Danziger, Moshav Mishmar Hashiva (IL)

(72) Inventor: Gabriel Danziger, Moshav Mishmar Hashiva (IL)

(73) Assignee: Danziger "DAN" Flower Farm, Moshav Mishmar Hashiva (IL)

( * ) Notice: Subject to any disclaimer, the term of this patent is extended or adjusted under 35 U.S.C. 154(b) by 0 days.

(21) Appl. No.: 14/121,801

(22) Filed: Oct. 20, 2014

(51) Int. Cl.
*A01H 5/02* (2006.01)

(52) U.S. Cl.
USPC ..... Plt./485

(58) Field of Classification Search
USPC ..... Plt./485
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of *Sutera* plant named 'Danova780', characterized by its compact, mounding and low spreading plant habit; moderately vigorous to vigorous growth habit; freely branching habit; early and freely flowering habit; and relatively large white-colored flowers.

1 Drawing Sheet

Botanical designation: *Sutera cordata.*
Cultivar denomination: 'DANOVA780'.

BACKGROUND OF THE INVENTION

The present invention relates to a new and distinct cultivar of *Sutera* plant, botanically known as *Sutera cordata* and hereinafter referred to by the name 'Danova780'.

The new *Sutera* plant is a product of a planned breeding program conducted by the Inventor in Moshav Mishmar Hashiva, Israel. The objective of the breeding program is to create new compact and freely branching *Sutera* plants with numerous large flowers.

The new *Sutera* plant originated from an open-pollination in March, 2010 in Moshav Mishmar Hashiva, Israel of a proprietary selection of *Sutera cordata* identified as code number 09-1202, not patented, as the female, or seed, parent with an unknown selection of *Sutera cordata* as the male, or pollen, parent. The new *Sutera* plant was discovered and selected by the Inventor as a flowering plant from within the progeny of the stated open-pollination in a controlled greenhouse environment in Moshav Mishmar Hashiva, Israel in November, 2010.

Asexual reproduction of the new *Sutera* plant by vegetative cuttings in a controlled greenhouse environment in Moshav Mishmar Hashiva, Israel since December, 2010, has shown that the unique features of this new *Sutera* plant are stable and reproduced true to type in successive generations.

SUMMARY OF THE INVENTION

Plants of the new *Sutera* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Danova780'.

These characteristics in combination distinguish 'Danova780' as a new and distinct *Sutera* plant:

1. Compact, mounding and low spreading plant habit.
2. Moderately vigorous to vigorous growth habit.
3. Freely branching habit.
4. Early and freely flowering habit.
5. Relatively large white-colored flowers.

Plants of the new *Sutera* can be compared to plants of the female parent selection. Plants of the new *Sutera* differ primarily from plants of the female parent selection in the following characteristics:

1. Plants of the new *Sutera* are more compact and mounding in plant habit than plants of the female parent selection.
2. Plants of the new *Sutera* are more freely branching than plants of the female parent selection.
3. Plants of the new *Sutera* flower earlier than plants of the female parent selection.
4. Plants of the new *Sutera* are more freely flowering than plants of the female parent selection.
5. Plants of the new *Sutera* have larger flowers than plants of the female parent selection.

Plants of the new *Sutera* can be compared to plants of the *Sutera* 'Dancop25', disclosed in U.S. Plant Pat. No. 19,747. In side-by-side comparisons conducted in Moshav Mishmar Hashiva, Israel, plants of the new *Sutera* differed primarily from plants of 'Dancop25' in the following characteristics:

1. Plants of the new *Sutera* were more compact and mounding in plant habit than plants of 'Dancop25'.
2. Plants of the new *Sutera* were more freely branching than plants of 'Dancop25'.
3. Plants of the new *Sutera* flowered earlier than plants of 'Dancop25'.
4. Plants of the new *Sutera* were more freely flowering than plants of 'Dancop25'.

Plants of the new *Sutera* can be compared to plants of the *Sutera* 'Dancop28', disclosed in U.S. Plant Pat. No. 21,551. In side-by-side comparisons conducted in Moshav Mishmar Hashiva, Israel, plants of the new *Sutera* differed primarily from plants of 'Dancop28' in the following characteristics:

1. Plants of the new *Sutera* were more mounding in plant habit than plants of 'Dancop28'.
2. Plants of the new *Sutera* were more freely branching than plants of 'Dancop28'.
3. Plants of the new *Sutera* and 'Dancop28' differed in flower color as plants of 'Dancop28' had light blue-colored flowers.

BRIEF DESCRIPTION OF THE PHOTOGRAPHS

The accompanying colored photographs illustrate the overall appearance of the new *Sutera* plant showing the colors as true as it is reasonably possible to obtain in colored reproductions of this type. Colors in the photographs may differ slightly from the color values cited in the detailed botanical description which accurately describe the colors of the new *Sutera* plant.

The photograph at the bottom of the sheet comprises a side perspective view of a typical flowering plant of 'Danova780' grown in a container.

The photograph at the top of the sheet is a close-up view of a typical flowering plant of 'Danova780'.

DETAILED BOTANICAL DESCRIPTION

The aforementioned photographs and following observations, measurements and values describe plants grown during the spring in 11.5-cm containers in an outdoor nursery in Bonsall, Calif. and under cultural practices typical of commercial *Sutera* production. During the production of the plants, day temperatures averaged 24° C., night temperatures ranged from 13° C. to 16° C. and light levels averaged 7,000 foot-candles. Plants were pinched two times and were six weeks from planting when the photograph and the description were taken. Plants were grown under long day/short night photoinductive conditions. In the description, color references are made to The Royal Horticultural Society Colour Chart, 2007 Edition, except where general terms of ordinary dictionary significance are used.

Botanical classification: *Sutera cordata* 'Danova780'.

Parentage:

*Female, or seed, parent*.—Proprietary selection of *Sutera cordata* identified as code number 09-1202, not patented.

*Male or pollen parent*.—Unknown selection of *Sutera cordata,* not patented.

Propagation:

*Type*.—By cuttings.

*Time to initiate roots, summer*.—About seven to ten days at temperatures ranging from about 18° C. to 32° C.

*Time to initiate roots, winter*.—About 10 to 15 days at temperatures ranging from about 13° C. to 26° C.

*Time to produce a rooted young plant, summer*.—About three weeks at temperatures ranging from about 18° C. to 32° C.

*Time to produce a rooted young plant, winter*.—About one month at temperatures ranging from about 13° C. to 26° C.

*Root description*.—Fine, fibrous; white in color.

*Rooting habit*.—Moderately freely branching; medium density.

Plant description:

*Plant and growth habit*.—Compact, mounded and low spreading plant habit; moderately vigorous to vigorous growth habit.

*Branching habit*.—Freely branching habit; when pinched, about twelve lateral branches develop per plant.

*Plant height*.—About 8 cm.

*Plant diameter* (*area of spread*).—About 28.5 cm.

Lateral branch description:

*Length*.—About 17 cm.

*Diameter*.—About 2 mm.

*Internode length*.—About 2 cm.

*Strength*.—Strong.

*Texture*.—Pubescent.

*Color*.—Close to 146A.

Leaf description:

*Arrangement*.—Opposite, simple.

*Length*.—About 1.8 cm.

*Width*.—About 1.7 cm.

*Shape*.—Orbicular.

*Apex*.—Rounded.

*Base*.—Attenuate.

*Margin*.—Crenulate.

*Texture, upper and lower surfaces*.—Sparsely pubescent.

*Venation pattern*.—Pinnate, arcuate.

*Color*.—Developing leaves, upper surface: Close to 146A. Developing leaves, lower surface: Close to 146B. Fully expanded leaves, upper surface: Close to 147A; venation, close to 147B. Fully expanded leaves, lower surface: Close to 137B; venation, close to 137B.

*Petioles*.—Length: About 4 mm. Diameter: About 2 mm. Texture, upper and lower surfaces: Sparsely pubescent. Color, upper surface: Close to 137A. Color, lower surface: Close to 137C.

Flower description:

*Flower arrangement*.—Single rotate and salverform flowers; freely flowering habit with potentially about 65 flower buds and flowers developing per lateral branch; flowers face mostly upright to outwardly.

*Fragrance*.—None detected.

*Natural flowering season*.—Early flowering habit, plants begin flowering about four weeks after planting and flower continuously from the spring until the autumn in southern California.

*Flower longevity*.—Flowers last about five to seven days on the plant; flowers persistent.

*Flower diameter*.—About 1.8 cm.

*Flower length* (*height*).—About 1.1 cm.

*Throat diameter*.—About 4 mm.

*Tube length*.—About 9 mm.

*Tube diameter, at the base*.—About 2 mm.

*Flower buds*.—Length: About 7 mm. Diameter: About 3 mm. Shape: Obovate. Color: Close to 145C.

*Petals*.—Quantity and arrangement: Five per flower in a single whorl; fused at the base. Lobe length: About 8 mm. Lobe width: About 8 mm. Lobe shape: Orbicular. Lobe apex: Obtuse, rounded. Lobe margin: Entire. Texture: Petal lobes, upper and lower surfaces: Smooth, glabrous. Throat: Pubescent. Tube: Pubescent. Color: Petal lobes, when opening, upper surface: Close to NN155D. Petal lobes, when opening, lower surface: Close to NN155B. Petal lobes, fully opened, upper and lower surfaces: Close to NN155D; venation, close to NN155D; color does not change with development. Throat: Close to 163A; venation, close to 157C. Tube: Close to 161B to 161C; venation, close to 157B.

*Sepals*.—Quantity and arrangement: Five per flower in a single whorl; fused at the base. Length: About 8 mm. Width: About 1 mm. Shape: Lanceolate. Apex: Acute. Margin: Entire. Texture, upper surface: Smooth, glabrous. Texture, lower surface: Pubescent; minute. Color, upper and lower surfaces: Close to 146A.

*Peduncles*.—Length: About 5 mm. Diameter: About 1 mm. Angle: About 30° from vertical. Strength: Strong. Texture: Pubescent; minute. Color: Close to 146B.

*Reproductive organs*.—Androecium: Quantity of stamens per flower: About four. Filament length: About 9 mm. Filament color: Close to 157D. Anther shape: Oval. Anther length: About 2 mm. Anther color: Close to 163B. Amount of pollen: Scarce. Pollen color: Close to 17C. Gynoecium: Pistil length: About 1.1 cm. Style length: About 9 mm. Style color: Close to 145D. Stigma shape: Rounded. Stigma color: Close to 145A. Ovary color: Close to 144A.

*Seeds & fruits*.—Seed and fruit production have not been observed on plants of the new *Sutera*.

Temperature tolerance: Plants of the new *Sutera* have been observed to tolerate temperatures from about 1° C. to about 35° C.

Pathogen & pest resistance: Plants of the new *Sutera* have not been shown to be resistant to pathogens and pests common to *Sutera* plants.

It is claimed:

1. A new and distinct *Sutera* plant named 'Danova780' as illustrated and described.

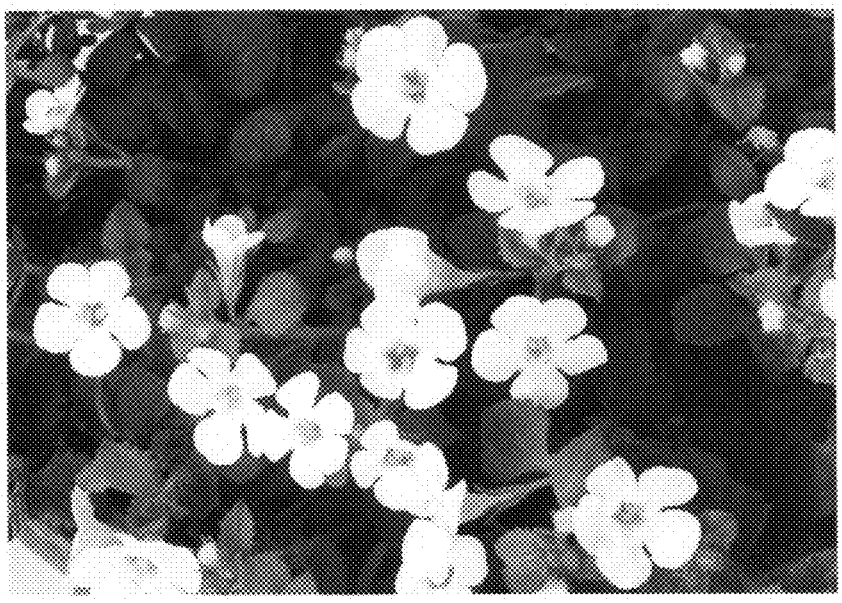
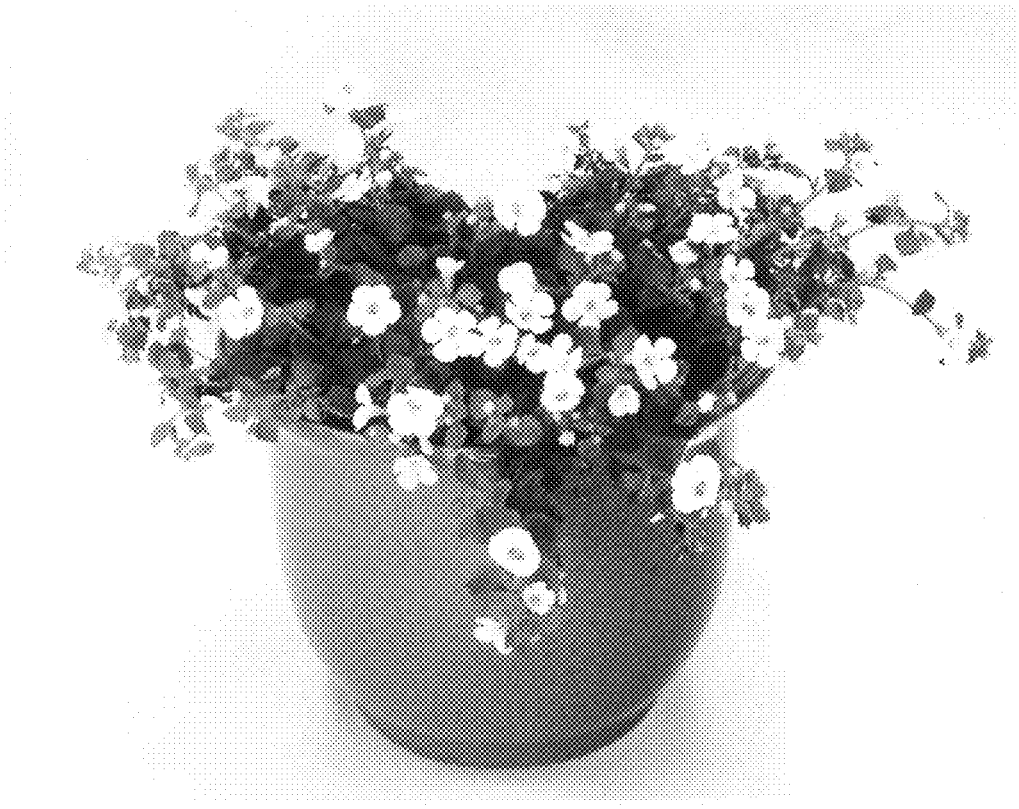

* * * * *